United States Patent [19]

Kim et al.

[11] Patent Number: 5,223,262
[45] Date of Patent: Jun. 29, 1993

[54] TRANSDERMAL DELIVERY SYSTEM UTILIZING ONE WAY MEMBRANES

[75] Inventors: Sung W. Kim, Salt Lake City, Utah; Teruo Okano, Chiba, Japan; Soon H. Yuk, Daejeon, Rep. of Korea

[73] Assignee: University of Utah, Salt Lake City, Utah

[21] Appl. No.: 565,479

[22] Filed: Aug. 10, 1990

Related U.S. Application Data

[63] Continuation-in-part of Ser. No. 314,156, Feb. 23, 1989, abandoned.

[51] Int. Cl.$^5$ .............................................. A61F 13/02
[52] U.S. Cl. .................................. 424/448; 424/449; 424/447; 428/413; 428/447
[58] Field of Search ..................... 424/448, 449, 447; 428/413, 447

[56] References Cited

U.S. PATENT DOCUMENTS

| | | | |
|---|---|---|---|
| 4,379,454 | 4/1983 | Campbell et al. | 424/449 |
| 4,820,720 | 4/1989 | Sanders et al. | 424/449 |
| 4,906,169 | 3/1990 | Chien et al. | 424/449 |
| 4,910,015 | 3/1990 | Sung et al. | 424/449 |

Primary Examiner—Thurman K. Page
Assistant Examiner—Leon R. Horne

[57] ABSTRACT

A system for transdermally delivering a hydrophobic alkanol soluble active agent to the skin at a constant rate utilizing a lower alkanol penetration enhancer. The system comprises an overlying solvent reservoir containing a lower alkanol solvent and a drug compartment containing an active agent in aqueous alkanol. A one-way membrane is sandwiched between and divides the solvent reservoir from the drum compartment. The one-way membrane is permeable to the alkanol solvent and substantially impermeable to back flux of drug and water into the reservoir. An outer membrane permeable to the alkanol solvent and drug is attached to the outer surface of the drug compartment. Adhesive means is contained on the outer surface of this membrane for attaching the delivery system to the skin of a wearer. Alkanol from the reservoir permeates into the drug compartment and drug and alkanol pass through the outer membrane to the skin of the wearer for transdermal absorption. The rate of alkanol permeation from the reservoir to the drug compartment and from the drug compartment to the skin is substantially constant. The membrane is made up of an epoxidized silicone rubber to which is preferably laminated a layer of a dense hydrophobic copolymer of vinyl-terminated polydimethyl siloxane with methylhydro-dimethyl siloxane. If desired, to prevent any back flux of hydrophobic drugs, and additional layer of cellulose acetate may be sandwiched between the epoxidized silicone rubber and dense hydrophobic membrane.

22 Claims, 1 Drawing Sheet

Fig. 1

TRANSDERMAL DELIVERY SYSTEM UTILIZING ONE WAY MEMBRANES

This application is a continuation-in-part of pending application Ser. No. 07/314,156 filed Feb. 23, 1989, now abandoned.

BACKGROUND OF THE INVENTION

This invention relates to transdermal drug delivery systems utilizing one-way membranes which permit a drug penetration enhancing solvent contained in an overlying reservoir to flow from the solvent reservoir into a drug containing compartment adjacent thereto but prevents significant back flow of water or drug into the solvent reservoir. More particularly, this invention relates to transdermal drug delivery systems utilizing novel one-way membranes which enable a lower alkanol solvent to flow from a solvent reservoir to a drug compartment at high solvent flux to assure a constant delivery of drug and penetration enhancing alkanol solvent to the skin of a patient.

The aim of a transdermal drug delivery system is to provide a continuous and relatively constant infusion of a medicinal agent across the skin for a prolonged period of time. There are numerous transdermal drug delivery systems taught in the art. Typical of the prior art relating to such systems are Chandrasekaran, et al., U.S. Pat. No. 4,201,211 (1980) "Therapeutic for Administering Clonidine Transdermally"; Campbell, et al. U.S. Pat. No. 4,379,454 (1983) "Dosage for Coadministering Drug and Percutaneous Absorption Enhancer"; Shaw, et al, U.S. Pat. No. 4,486,193 (1984) "Method for Treating Ischemic Conditions by Administering Drug by Two Routes"; Gale, et al, U.S. Pat. No. 4,588,580 (1986) "Transdermal Administration of Fentanyl and Device Therefor" and Gale et al., U.S. Pat. No. 4,681,584 (1987) "Transdermal Delivery System for Delivering Nitroglycerin at High Transdermal Fluxes".

The permeation of many drugs is limited by the skin. The resistance of the skin to being penetrated by medicinal agents is well documented. As compared to mucosal tissues, the stratum corneum is compact and highly keratinized and quite impermeable. Such impermeability of the skin is highly essential to the well being of a living organism in that it serves as a barrier to the ingress of pathogens and toxic materials, and the egress of physiologic fluids.

The impermeability of medicinal agents through the skin is due to the nature of the very thin stratum corneum layer which is only 10-15 cells, i.e. about 10 microns thick. This layer is formed naturally by cells migrating toward the skin surface from the basal layer. Cells slowly move from the basal layer to the surface where they are sloughed off. As the progress toward the surface they become progressively more dehydrated and keratinized.

Because of the advantages of dermal application of drugs or other medicinal agents, various penetration enhancers have been sought. A penetration enhancer is one or more compounds which alter the skin as a barrier to increase the flux of a desired drug across the skin layer. One class of enhancers is solvents. The co-delivery of drug and solvent, such as lower alkanols, to increase skin transport is a major concern in the design of effective transdermal delivery systems. See for example, Durrheim, et al., J. Pharm. Sci., 69, (1980) 781-786; Ghanem, et al., J. Controlled Release, 6 (1987) 75-83 and Barry, J, Controlled Release, 6, (1987) 85-97. It is known that an ethanol permeation rate of 800 ug/cm$^2$/hr can aid in the permeation of some drugs across the skin barrier. This use of a lower alkanol such as ethanol, propanol or isopropanol in a transdermal delivery device is twofold. First, alkanol acts as a permeation enhancer. Second, it also aids in solubilizing the drugs.

In conventional membrane-based transdermal delivery systems the solvent and the drum, at saturation, reside in a single reservoir from which the delivery of both components to the skin is controlled by the outer membrane separating the system from the skin. This design has certain inherent deficiencies. Hydration of the skin affects drug transport. Consequently, the activities of solvent, such as an alkanol, and water must be optimized at the skin surface. This multicomponent enhancer deliver problem is particularly difficult if the drug and solvent flux are controlled by the same membrane. Since the reservoir does not usually contain water, the hydration is caused by water being delivered to the skin surface from beneath the stratum corneum. In any delivery system containing an alkanol solvent reservoir, whether separate or combined with the drug compartment, if water from beneath the skin and drug, from the drug compartment, can permeate into the alkanol solvent reservoir there will be a mixing of alkanol, water and drug in the solvent with the resultant decrease of drug concentration in the drug donor chamber. This obviously causes a decrease in the drug concentration adjacent the skin and lowers the drug flux. Also, in many systems the permeation rate of the solvent across the skin is often higher than that of the drug. In this situation, the transdermal delivery may fail to sustain drug release due to the rapid depletion of solvent from the system.

Another problem which may arise is the cost. When the drug is expensive and highly soluble in the enhancing solvent, the necessity of incorporating the drug into the reservoir can make the cost of the transdermal system impractical.

It would therefore be desirable to have a delivery system with permitted the permeation of alkanol from a separate solvent reservoir but prevented the back permeation of water and/or drug from a drug donor chamber into a solvent reservoir. Such as delivery system would require the presence of a membrane barrier which would allow solvent diffusion while preventing back diffusion of water and solute. This membrane could appropriately be categorized as a one-way diffusion membrane.

Existing polymeric materials are not suitable for such purposes. For example, a 2 mil low density polyethylene (PE) membrane will transmit ethanol at only 23 ug/cm$^2$/hr, but has an ethanol-water selectivity ratio of 19, e.g., the ratio of their respective fluxes. For a suitable one-way membrane the selectivity ratio should be high. A higher ethanol flux may be obtained by incorporating vinyl acetate into the PE. A 2 mil PE membrane containing 9% vinyl acetate has an ethanol flux of about 400 ug/cm$^2$/hr but the selectivity ratio decreased to about 8. If the vinyl acetate content is increased to about 40%, the ethanol flux increases to 7.5 mg/cm$^2$/hr, but the selectivity ratio drops to 2.3.

Certain silastic polymers (silicone rubbers) are significantly better. A typical silastic polymer 2 mil membrane has an ethanol flux of about 450 ug/cm$^2$/hr and an ethanol to water selectivity ratio greater than 50.

OBJECTS AND BRIEF SUMMARY OF THE INVENTION

It is an object of the present invention to provide a modified silastic polymer membrane which alleviates the difficulties of the traditional membrane drug delivery systems.

It is also an object of this invention to provide a two-compartment delivery device in which an enhancing alkanol solvent is allowed to pass from a solvent reservoir through a one-way membrane into a drug containing compartment from which both solvent and drug are delivered to the skin surface.

A still further object of the invention is to provide a novel modified silastic polymer membrane which separates a solvent reservoir from a drug containing compartment in the system and allows solvent to enter the drug compartment at an acceptable rate but prevents significant back diffusion of the drug and water into the solvent reservoir.

Another object of the invention is to provide a transdermal drug delivery system enabling simultaneous control of an alkanol solvent and water activity at the skin surfaces by keeping the alkanol activity in the drug compartment constant at lower drug content while preventing drug flux into an overlying alkanol reservoir.

These and other objects may be accomplished by a novel delivery system comprising an overlying or upper solvent reservoir and an underlying drug containing compartment separated by a novel epoxy silicone rubber containing membrane which is impermeable to the drug but which allows the passage of solvent from the solvent reservoir into the drug compartment over a prolonged period of time.

The membrane may be a single layer but is preferably a bilaminate of two silicone rubbers of a trilaminate of two silicone rubbers and a hydrophilic water impermeable cellulose acetate polymer. The base membrane is a copolymer of a silicone rubber, such as a polydimethylsiloxane, and an epoxide, such as a polyglycerol-polyglycidyl ether. The bilaminate is a layer of the base membrane and a layer comprising a dense hydrophobic copolymer of vinyl-terminated polydimethyl siloxane with methylhydro-dimethyl siloxane. By "dense" is meant that no pore or pore mechanism exists in the membrane. The trilaminate differs from the bilaminate in that a cellulose acetate membrane exists between the epoxy silicone rubber base membrane and the dense hydrophobic silicone rubber membrane.

The role of the epoxide containing silastic polymer membrane is to enhance alkanol permeability by altering the membrane solubility parameter toward ethanol and preventing water back flux. The bilaminate vinyl-terminated polydimethyl siloxane/methylhydro-dimethyl siloxane copolymer has excellent water repellency due to its hydrophobic crosslinked network and provides permselectivity of ethanol over water. Alkanol permeation through the trilaminate membrane is similar to the bilaminate membrane. However, the hydrophilic cellulose acetate layer provides additional hydrophilicity to the membrane to exclude permeation of more lipophilic solutes (drugs) such as estradiol or testosterone.

The system comprises an overlying solvent reservoir and an underlying drug compartment separated by the above described one-way membrane. When using a bilaminated or trilaminated membrane, the base membrane faces the solvent reservoir and the dense hydrophobic membrane faces the drug compartment. On the opposite side of the drug compartment is secured an outer membrane which contains adhesive means to affix the system to the skin. The one-way membrane system provides high alkanol flux from the overlying reservoir through the one-way membrane into the drug compartment with minimal water flux from the drug compartment back to the solvent reservoir. Additionally, there is no drug or solute flux from the drug compartment to the solvent reservoir. In operation, the driving force is from the alkanol solvent reservoir allowing an alkanol to enter into the drug compartment where drug is solubilized in the alkanol providing adequate and prolonged drug and alkanol flux through the outer membrane and across the skin barrier. In other words, the operable flux is across the one-way membrane for the delivery of alkanol to the drug compartment and the concurrent flux of drug and alkanol across the outer membrane to the skin.

DETAILED DESCRIPTION OF THE INVENTION

Figure 1:
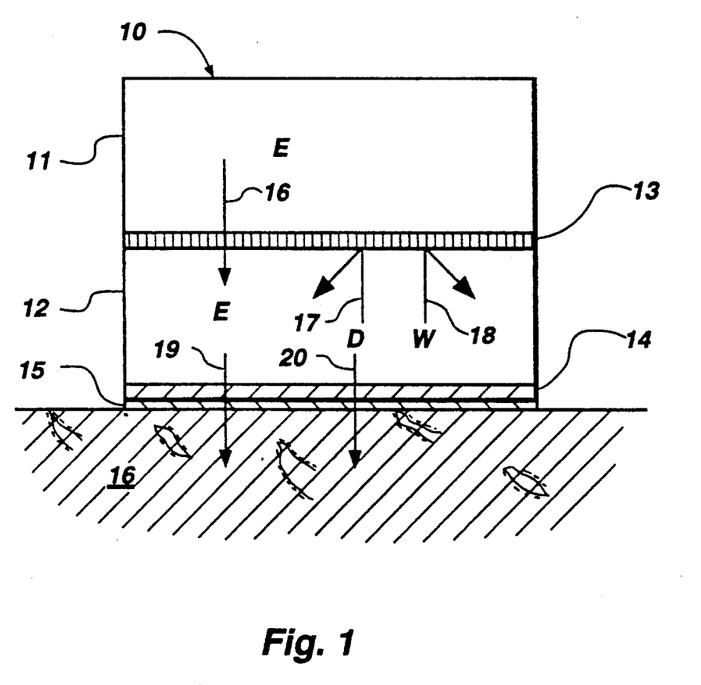
FIGURE 1 is a schematic side view of a transdermal system showing the positioning of the overlying solvent reservoir, the one-way membrane, the drug compartment and outer membrane with adhesive attachment means.

There is shown in FIG. 1 a representative embodiment of a transdermal drug delivery system utilizing a one-way membrane for the delivery of an alkanol solvent from an overlying reservoir to a drug containing compartment where the alkanol is maintained at a relatively constant concentration and from which an effective amount of a drag, soluble in the alkanol, can permeate through the skin of a subject being treated with the drug.

The system 10 (which would also properly be called a device, patch or other similar term) consists of an overlying solvent reservoir 11 having one unenclosed surface and an underlying drug containing compartment 12 having opposing unenclosed surfaces. Attached to the unenclosed surface of reservoir 11 and to one surface of drug compartment 12 thereby dividing reservoir 11 from compartment 12 is a one-way membrane 13. On the opposing unenclosed surface of drug compartment 12 is an outer membrane 14 containing adhesive means 15 for securing the system 10 to the skin 16 of a wearer. A solvent and drug impermeable peelable cover (not shown) may cover the adhesive layer 15 prior to use to prevent the discharge of drug and/or solvent from the system during storage.

In operation, solvent E from reservoir 11 permeates one-way membrane 13 into drug compartment 12 as shown by arrow 16 and is symbolically referred to herein as $P_{E1\text{-}2}$. The one-way membrane 13 is constructed such that drug D and water W contained in drug compartment 12 will not back flux or permeate into solvent reservoir 11 as indicated by arrows 17 and 18. This is symbolically referred to herein as $P_{D2\text{-}1}$ and $P_{W2\text{-}1}$ respectively. The drug D is soluble in lower alkanol solvent E but is usually not soluble in water W. In other words, the present invention is more applicable to the delivery of hydrophobic drugs soluble in the alkanol solvent than to the delivery of hydrophilic drugs. However, the alkanol solvent will generally be an aqueous alkanol solvent as will be described. Hence, compartment 12 will contain alkanol solvent E, drug D and water W. The lower alkanol E serves as a skin penetration enhancer as well as a solvent. Hence, solvent E and drug D penetrate the outer membrane 14 and adhesive layer 15 and enter the skin as illustrated by arrows 19 and 20 respectively. Symbolically this is referred to herein as $P_{E2-3}$ and $P_{D2-3}$. Preferably $P_{E1-2}$ and $P_{E2-3}$ will be at about the same rates to keep the concentration of E in drug compartment 12 constant.

Function and Preparation of One-Way Membranes

The silicone rubbers used in this invention are primarily copolymers of polydimethylsiloxane which are synthesized and characterized for their lower alkanol and water transport properties. To allow high alkanol fluxes ($P_{E1-2}$), the selectivity of the base membrane is combined with the high alkanol swelling properties of epoxides. A bilaminate membrane is preferred over the single base layer in that the second membrane layer controls the water flux at a low level. This is accomplished by the synthesis of a dense hydrophobic silastic copolymer membrane prepared by copolymerizing a methylhydrodimethylsiloxane coplymer with a polydimethylsiloxane. The trilaminate is preferred for use with drug solutes of varying hydrophobicity in that the third membrane layer of cellulose acetate is highly hydrophilic and inhibits passage of hydrophobic solutes ($P_{D2-1}$). By proper combination of the various laminate layers it is possible to structure a true one-way membrane suited to the purpose of allowing the flux of solvent in one direction ($P_{E1-2}$) while prohibiting the passage or back flux of water and drug solute ($P_{D2-1}$ and $P_{W2-1}$) into the solvent reservoir.

Base Membrane

A cross-linked epoxidized silicone rubber was obtained by combining a copolymer of polydimethyl siloxane (SR) and a polyglycerol-polyglycidyl ether (EP) as follows:

Vulcanization is complete within about two hours when cured at 70° c.

When used as a single one-way membrane the typical film thickness is about 0.6 mm. When used for preparing bilaminates or trilaminates the thickness of typically about 0.4 mm.

Instead of being cast on a Teflon plate, the polymer blend can be cast on other membranes, i.e. on a cellulose acetate membrane when being used to prepare a trilaminate membrane or on a hydrophobic silastic when being used to prepare a bilaminate membrane. However, it may be preferred to cast the hydrophobic silastic on the base membrane instead of the other way around.

Bilaminate Membrane

A dense hydrophobic silicone rubber membrane for lamination to the base membrane is prepared in the same manner as the base membrane by blending a vinyl-terminated polydimethyl siloxane [VTPDS] with a methylhydro-dimethyl siloxane copolymer [MH-DMS-CP] and then casting or spreading the blend on a the surface of the base membrane where it is allowed to cure. If desired, the hydrophobic membrane could first be prepared and cast on a Teflon plate or similar non-adhering surface and the base membrane could then be cast on the surface of the hydrophobic membrane.

The following formula exemplifies a simplified embodiment of a hydrophobic membrane polymer:

Formula 2

Formula 1 wherein y is a numeral of about 2 to 222 with 13 to 222 being preferable, z is an integer of 2 or 3, PDMS stands for a poly dimethyl siloxane silicone rubber and EP is an epoxide and particularly a polyglycerol-polyglycidyl ether. PDMS makes up about 90 to 98% w. of the polymer and EP is present in amounts of between about 2 to 10% w. The PDMS may be any suitable poly dimethyl siloxane including vinyl terminated poly dimethyl siloxane (VTPDMS).

The PDMS-EP polymer is prepared by blending the silastic rubber and glycidyl ether compounds thoroughly to ensure a uniform blend and cure. The blended mixture is then spread as a film on a non-adhering surface such as a polytetrafluoroethylene (Teflon) plate to a uniform thickness with a doctor's knife and cured.

-continued wherein m, n, x and y have the meanings given above. This formula is an example only. The moieties which occur m, n, x and y times are located in random fashion and the cross linking may occur at different places. Therefore, the formula is only representative of a typical dense hydrophobic silastic polymeric matrix which can be formed. The silastic blend consists of about 90 to 98% w. of the vinyl-terminated polydimethyl siloxane and about 2 to 10% w. of the methylhydro-dimethyl siloxane copolymer. When casting the hydrophobic silastic polymer on the base membrane the relative thickness of the two sheets preferably will not exceed about 0.4 to 1.0 mm with about 0.6 mm being optimal. The relative thickness of each layer can vary somewhat but the base sheet will generally be thicker than the hydrophobic membrane sheet by a ratio of about 2:1. In other words, a base membrane of about 0.4 mm and a hydrophobic membrane of about 0.2 mm is about optimal.

Trilaminate Membrane

The trilaminate membrane is prepared by first casting cellulose acetate in acetone on a glass plate and evaporating the acetone in a closed system. Cellulose acetate film thickness is controlled by the concentration of cellulose acetate. When casting for the present examples the cellulose acetate was first dissolved in 50 mls of acetone and cast on a 400 cm² plate. For films 10 microns thick 2 grams of cellulose acetate were used per 50 mls of acetone and for films 40 microns thick 4.5 grams of cellulose acetate were dissolved in 50 mls of acetone.

Once the cellulose acetate films was formed by evaporation of the acetone, trilaminate membranes were formed by casting the base membrane and hydrophobic membrane on either side of the cellulose acetate film. In other words, the cellulose acetate film was sandwiched between the base and hydrophobic membranes.

The following examples illustrate the preparation of various base, bilaminate and trilaminate one-way membranes.

EXAMPLE 1

A series of base membranes were prepared by casting onto a Teflon plate according to the procedures outlined above. Each membrane was cast having a thickness of 0.6 mm. Membrane A2 was also cast with a thickness of 0.4 mm. With reference to Formulas 1 and 2, the following table shows the composition of each membrane in percent by weight of each component.

TABLE A

| Membrane No. | PDMS | EP | z | MH-DMS-CP |
|---|---|---|---|---|
| A1 | 95 | 5 | 2 | — |
| A2 | 95 | 5 | 3 | — |
| A3 | 95 | — | — | 5 |
| A4 | 98 | 2 | 2 | — |
| A5 | 99 | 1 | 2 | — |
| A6 | 100 | — | — | — |

PDMS is Silastic Q7-4840 (Dow Corning Medical grade vinyl terminated poly dimethyl siloxane); EP, where z = 2, is Denacol 512 and EP, where z = 3, is Denacol 521 (Nagase Chemical Ltd. brand of polyglycerol-polyglycidyl ethers); MH-DMS-CP is methylhydrodimethyl siloxane (30/70/w/w) copolymer (from Petrarch Systems).

EXAMPLE 2

Onto the surface of the 0.4 mm thick A2 membrane was cast a 0.2 mm layer of membrane A3 where it was allowed to cure to form a bilaminate membrane having a thickness of 0.6 mm. For purposes of reference, this membrane has been designated Membrane B.

EXAMPLE 3

Trilaminate membranes C1 and C2 were prepared using Membranes A2 and A3 as outer layers with a layer of cellulose acetate (Aldrich Chemical) having thicknesses of 10 and 40 microns respectively, sandwiched between. These membranes were prepared in the manner given above by casting 2 and 4.5 grams of cellulose acetate respectively in 50 mls of acetone on a 400 cm² plate and evaporating the acetone in a closed system. Membranes A2 and A3 were then cast on either side of the cellulose acetate films and cured to give membranes C1 and C2 having thicknesses of 0.61 mm and 0.64 mm respectively.

EXAMPLE 4

Membrane swelling measurements were performed as a function of the aqueous ethanol composition to show alkanol permeation capabilities. Membrane A1 was selected as the reference membrane for a swelling behavior of a silicone rubber. Swelling, as a percent of the dehydrated polymer, was measured by the following equation:

$$\% \text{ Swelling} = (W_s - W_o)/W_o \times 100$$

where $W_s$ is the weight of the swollen polymer and $W_o$ is the weight of the dehydrated polymer. The swelling in various membranes as a function of ethanol concentration in aqueous ethanol is given in Table B:

TABLE B

| % Swelling Membrane | | | | |
|---|---|---|---|---|
| A2 | A1 | A4 | A5 | % V EtOH |
| 1.2 | 0.6 | 0.3 | 0.2 | 0 |
| 1.3 | 0.7 | 0.3 | 0.3 | 10 |

TABLE B-continued

| % Swelling Membrane | | | | |
|---|---|---|---|---|
| A2 | A1 | A4 | A5 | % V EtOH |
| 1.4 | 0.7 | 0.3 | 0.3 | 20 |
| 1.5 | 0.8 | 0.3 | 0.3 | 30 |
| 2.0 | 0.9 | 0.4 | 0.3 | 40 |
| 2.5 | 1.0 | 0.4 | 0.3 | 50 |
| 2.7 | 1.1 | 0.5 | 0.4 | 60 |
| 3.2 | 1.6 | 0.6 | 0.3 | 70 |
| 3.9 | 1.8 | 0.7 | 0.4 | 80 |
| 4.4 | 2.6 | 1.4 | 0.6 | 90 |
| 10.0 | 6.2 | 4.4 | 2.4 | 100 |

A standard hydrogen polymer such as poly (2-hydroxyethyl methacrylate) [HEMA], and derivatives exhibit a maximum swelling which is indicative of poor permselectivity between ethanol and water. One reason for such poor permselectivity is because the solubility parameter (cal/cm$^3$)$^{\frac{1}{2}}$ of HEMA is intermediate between that of ethanol and water. The PDMS polymers, with or without the epoxide (EP), increase in swelling monotonically with ethanol concentration. This is consistent with the solubility parameter of PDMS (7.35) being less than that of ethanol (12.92) or water (23.5) but being closest to ethanol. This is in agreement with silicone rubber being the most permselective polymer for ethanol over water. The solubility parameter of the EP (polyglycerolpolyglycidyl ethers) used in the membranes is approximately equal to that of propylene glycol (14.8) which is also close to that of ethanol. It might therefore be expected that their addition would improve the permselectivity of the membranes for ethanol but this was not the case. While the total ethanol swelling increases dramatically with EP content, the ratio of ethanol:water swelling remains nearly constant at approximately 12. Membrane A2, wherein the EP has an extra molecular segment (see Formula 2 wherein z=3) showed greater swelling than membrane A1 wherein z=2. However, the selectivity of A2 is not statistically different from A1 as reflected by the ratio of swelling of about 8.

The use of the EP therefore becomes a method of controlling the total ethanol and water fluxes but not the permselectivity for ethanol.

EXAMPLE 5

The preferential uptake of ethanol from aqueous ethanol solutions into silicone rubber polymers, with and without EP being present, was analyzed by the sorption-desorption method. The membranes A2 and A6 were cast as in Example 1 to be 0.1 mm in thickness. They were then fabricated as discs (0.5 cm diameter and 0.1 thick) and immersed in aqueous ethanol containing $^{14}$C-ethanol and $^3$H$_2$O. After sorption occurred, the discs were placed in pure water for three days. The amounts of $^{14}$C-ethanol and $^3$H$_2$O released from the membranes were quantized by scintillation counting using the scintillation cocktail, Ecosint A [National Diagnostic, Mansville, N.J.] with the results as shown in Table C.

TABLE C

| % EtOH in Membrane Membrane | | |
|---|---|---|
| A2 | A6 | % V EtOH |
| 38 | 47 | 10 |
| 61 | 74 | 20 |
| 63 | 82 | 40 |

TABLE C-continued

| % EtOH in Membrane Membrane | | |
|---|---|---|
| A2 | A6 | % V EtOH |
| 72 | 84 | 60 |
| 78 | 86 | 80 |
| 100 | 100 | 100 |

The preference for ethanol shown above is reflected by the ratio of the concentration of ethanol in the membrane to that of ethanol in the surrounding aqueous ethanol solution. Even at 20 v % ethanol in solution, ethanol predominates in these membranes. This preference for ethanol results from the solubility parameters mentioned above and should be indicative of the permselectivity for ethanol. At lower concentrations, the uptake of ethanol into the membranes increases as ethanol concentration increases up to about 20 v % and then increases more slowly beyond that point.

EXAMPLE 6

To investigate the one-way diffusion of ethanol through the membranes a two compartment glass diffusion cell was utilized. Each compartment had a volume of 8.0 mls. Compartment 1 (comparable to reservoir 11 of FIG. 1) was filled with $^{14}$C-ethanol in the neat ethanol and compartment 2 (comparable to compartment 12 of FIG. 1) was filled with $^3$H$_2$O in deionized water. The chambers were connected via a 0.6 mm thick membrane (comparable to one-way membrane 13 of FIG. 1) having a surface area of 1.77 cm$^2$. 100 ul samples were withdrawn from the compartments at fixed time intervals and were analyzed by scintillation counting for the presence of ethanol in the water chamber to determine flux of ethanol and for water in the ethanol chamber to determine flux of water. The ethanol and water flux, according to the EP content in the membrane is recorded in Table D.

TABLE D

| Membrane | EP Content | Flux ($10^{-2}$ ml/cm$^2$/hr) | |
|---|---|---|---|
| | | EtOH | Water |
| A6 | 0% | 0.8 | 0.1 |
| A5 | 1 | 1.3 | 0.2 |
| A4 | 2 | 1.4 | 0.25 |
| A1 | 5 | 1.7 | 0.3 |
| A2 | 5 | 1.9 | 0.5 |

As can be seen, the ethanol flux increases with EP content. However, the selectivity is not statistically different between the various membranes. Membrane A2, containing the higher molecular weight EP, exhibits an increased ethanol flux over A1 which has the same EP percent but contains the lower molecular weight EP and also has a higher selectivity, 12, then A1. It appears that the silicone rubber portion of the membrane is the dominant polymer in the permeation behavior of these membranes in that there is no statistical difference in the permeation of ethanol or water through equal thickness silastic membranes with or without EP content. In other words, within the range shown, the permeation of ethanol and water is independent of EP content. Therefore, the addition of EP to the silicone rubber is primarily beneficial in obtaining small increases in fluxes without comprising selectivity.

When considering ethanol flux, membrane A2 has the greatest flux and will be used in the following examples in the testing of bilaminate and trilaminate membranes.

EXAMPLE 7

Membranes B (0.6 mm thick) and C2 (0.64 mm thick) were prepared as in Examples 2 and 3 and used to demonstrate the improvement which can be obtained in lowering water flux by using a bilaminate or trilaminate membrane over the use of a single A2 membrane alone while retaining the ethanol flux. Membrane B is a bilaminate of A2 and the dense hydrophobic A3 membrane. This membrane has excellent water repellency due to its hydrophobic cross-linked network but still permits the flux of ethanol. Membrane C2, which has a 40 micron layer of cellulose acetate sandwiched between membranes A2 and A3, has negligible resistance to ethanol flux, and is comparable in ethanol and water flux to Membrane B. Tests were run according to Example 6 above using either $^{14}C$-ethanol in neat ethanol or $^3H_2O$ in deionized water placed in compartment 1 and various concentrations of aqueous ethanol placed in compartment 2. Samples were withdrawn from compartment 2 at intervals and tested as in Example 6. The results of these tests are given in Table E.

TABLE E

| % EtOH in Chamber 2 | EtOH Flux ($10^{-2}$ ml/cm$^2$/hr) Membrane | | | Water Flux ($10^{-3}$ ml/cm$^2$/hr) Membrane | | |
|---|---|---|---|---|---|---|
| | A2 | B | C2 | A2 | B | C2 |
| 0 | 1.9 | 1.9 | 1.8 | 5.4 | 1.8 | 1.8 |
| 10 | 2.7 | 2.2 | 1.9 | 6.5 | 1.5 | 1.4 |
| 20 | 2.9 | 2.4 | 2.2 | 7.8 | 1.9 | 1.8 |
| 30 | 3.4 | 2.8 | 2.3 | 8.7 | 2.3 | 2.2 |
| 40 | 3.4 | 3.0 | 2.6 | 9.0 | 2.4 | 2.3 |

The above shows permeation as a function of ethanol composition in aqueous ethanol compartment 2. For ethanol in compartment 1, the flux of $^{14}C$-ethanol is at a fixed driving force. Therefore, only the effects of ethanol concentrations on the membranes are reflected. Water permeation, however, is at a reduced driving force with increasing ethanol concentration in compartment 2. As shown by the ethanol flux, ethanol permeation increases with ethanol concentration up to about 40 v % ethanol. Above that, the flux plateaus. This reflects the ethanol swelling and preference of the membrane for ethanol. Water permeation, as shown above, also increases somewhat with increasing ethanol content but also plateaus above about 40 v %. This is also indicative of permeation through the ethanol phase swelling the matrix. However, note the decreased water flux through membranes B and C2 as compared with A2.

While the above examples establish the ability of the membranes, and particularly the bilaminate and trilaminate membranes, to be selectively permeable to lower alkanols ($P_{E1-2}$), such as ethanol, as compared to water ($P_{H2-1}$), they do not show the impermeability of a system utilizing such one-way membranes to prevent back flux of active drug or solute ($P_{D2-1}$) into a solvent reservoir separated from the drug compartment by such a membrane. The following examples are illustrative of such properties.

EXAMPLE 8

This example illustrates the propensity of hydrophobic drugs, such as estradiol, and more hydrophilic drugs, such as hydrocortisone, to permeate the epoxidized silicone rubber membrane A2. In this test the two compartment permeation cells utilized in the above examples was again employed. Compartment 1 was filled with neat ethanol and compartment 2, containing the drug, was tested at various aqueous ethanol concentrations. Tritiated estradiol ($^3H$-estradiol) or hydrocortisone ($^3H$-hydrocortisone) was placed in compartment 2 in the aqueous ethanol at the given concentration. A single time point of 5 days was used as the equilibration time since this time mimics equilibration of a packaged transdermal product. The results of drug permeation into compartment 1 from compartment 2 are shown in Table F:

TABLE F

| v% EtOH | mg Drug Comp. 2 (initial) $C_{di}$ | mg Drug Comp. 1 (at equilibrium) $C_{re}$ | $C_{re}/C_{di}$ |
|---|---|---|---|
| Estradiol | | | |
| 0 | $4.40 \times 10^{-4}$ | $1.77 \times 10^{-4}$ | 0.402 |
| 10 | $2.34 \times 10^{-3}$ | $7.20 \times 10^{-4}$ | 0.308 |
| 20 | $1.63 \times 10^{-2}$ | $5.20 \times 10^{-3}$ | 0.319 |
| 30 | $4.68 \times 10^{-1}$ | $1.58 \times 10^{-1}$ | 0.338 |
| 40 | 1.98 | $8.31 \times 10^{-1}$ | 0.420 |
| Hydrocortisone | | | |
| 0 | $7.20 \times 10^{-2}$ | $7.68 \times 10^{-4}$ | 0.011 |
| 10 | $6.25 \times 10^{-1}$ | $1.13 \times 10^{-3}$ | 0.002 |
| 20 | 1.22 | $2.54 \times 10^{-3}$ | 0.002 |
| 30 | 4.00 | $6.41 \times 10^{-3}$ | 0.002 |
| 40 | 6.25 | $7.17 \times 10^{-3}$ | 0.001 |

As can be seen, permeation of estradiol does not increase monotonically with ethanol content. Consequently, polymer-solute (drug) interactions dominate transport as opposed to permeation through the swollen ethanol phase of the matrix. It can also be seen that the more hydrophobic agent, estradiol, permeates the membrane more easily than the more hydrophilic hydrocortisone. The permeation of hydrocortisone through membrane A2 is minimal. Increasing lipophilicity appears to improve permeation through this membrane.

One of the criteria for a suitable one-way membrane is the absence of solute (drug) back permeation ($P_{D2-1}$) into the solvent reservoir. For hydrophilic drugs, the dense hydrophobic membrane A3 or membrane B (a combination of membranes A2 and A3), may be appropriate because they are essentially impermeable to hydrophilic solutes. However, additional hydrophilicity may be necessary in a one-way membrane to exclude back flux of more lipophilic solutes such as estradiol or testosterone. This additional hydrophilicity cannot occur in the bilaminate layers, because the permselectivity for the lower alkanol would decrease. Therefore, an additional hydrophilic layer, cellulose acetate, is added to form a trilaminate which inhibits the back flux of the more lipophilic solutes. This feature is shown in the following example.

EXAMPLE 9

The ability of hydrophobic drugs estradiol and testosterone to permeate bilaminate and trilaminate membranes are shown. Membrane B is a bilaminate consisting of 0.4 mm layer of membrane A2 and 0.2 mm of a layer of A3. Membrane C1 is a trilaminate of a 10 micron layer of cellulose acetate sandwiched between a 0.4 mm layer of membrane A2 and a 0.2 mm layer of A3. Membrane C2 differs from C1 only in that the cellulose acetate layer is 40 microns thick. Samples of 1 mg of tritiated estradiol or testosterone were placed in compartment 2 in 40 v % ethanol and at time intervals of 6, 12, 24, 36, 48, 60 and 72 hours, samples were withdrawn from compartment 1 and analyzed by scintillation counting to determine the amount of drug which had permeated the membranes. The results are shown in Table G:

TABLE G

| Drug Membrane | $P_{D2-1}(10^{-1}$ milligrams) | | | | | |
|---|---|---|---|---|---|---|
| | Estradiol | | | Testosterone | | |
| | B | C1 | C2 | B | C1 | C2 |
| Time (Hours) | | | | | | |
| 0 | 0.0 | 0.0 | 0.0 | 0.0 | 0.0 | 0.0 |
| 6 | 0.2 | 0.05 | 0.0 | 0.4 | 0.1 | 0.0 |
| 12 | 0.7 | 0.1 | 0.0 | 0.9 | 0.2 | 0.0 |
| 24 | 1.6 | 0.2 | 0.0 | 1.7 | 0.4 | 0.0 |
| 36 | 2.5 | 0.3 | 0.0 | 3.6 | 0.7 | 0.0 |
| 48 | 3.9 | 0.5 | 0.0 | 4.8 | 0.9 | 0.0 |
| 60 | 4.2 | 0.6 | 0.0 | 5.1 | 1.1 | 0.0 |
| 72 | 4.3 | 0.7 | 0.0 | 5.2 | 1.2 | 0.0 |

Since the layer of cellulose acetate in membranes C1 and C2 does not materially affect either ethanol or water permeation, it also does not alter the solvent gradients within the A2 and A3 layers on either side. However, as shown in the above table, estradiol and testosterone permeation is markedly reduced by the presence of a 10 micron cellulose acetate membrane when one compares the results of membrane B with membrane C1. Membrane C2, having a 40 micron layer of cellulose acetate reduced estradiol and testosterone permeation to undetectable levels as indicated in the table. Such a drastic reduction is unexpected from a series resistance viewpoint and solvent gradient effects cannot explain the results. Since time lags can become excessively long, both estradiol and testosterone permeation were measured through membrane C2 after exposure for 30 days. No permeation of either drug was observed. Based on these results it can be seen that the C1 and C2 trilaminate membranes are suitable one-way membranes in preventing back flux of hydrophobic drugs.

The above examples establish the ability of the one-way membranes, and particularly the bilaminate and trilaminate membranes, to be selectively permeable to lower alkanols, such as ethanol, as compared to water and also show the impermeability of a system utilizing such one-way membranes in preventing the back flux of active drug or solute into a solvent reservoir separated from the drug compartment by such a membrane.

The following examples now focus on the ability of a delivery system utilizing a one-way membrane to deliver drugs at an acceptable and consistent flux ($P_{D2-3}$) to the skin of a user. A three compartment glass permeation cell, similar to the two compartment cell in the above studies, was used in the following examples. This cell consisted of three cylindrical compartments having a cross sectional area of 1.77 cm². Compartment 1 is the solvent compartment or solvent reservoir (comparable to reservoir 11 in FIG. 1) and is separated from compartment 2 by a one-way membrane (membrane 13 in FIG. 1). Unless otherwise stated the membrane is the trilaminate membrane C2. Compartment 2 (comparable to drug compartment 12 in FIG. 1) contains the drug being tested in various concentrations of aqueous ethanol. Compartment 2 is divided from compartment 3 by a membrane (comparable to membrane 14 in FIG. 1) which, in actual use, would be in contact with the skin (numeral 16 of FIG. 1) of a user. Three membranes (Membranes I, II and III) were utilized in the examples and will be described in greater detail below. Compartment 3 serves as a receiving compartment for the permeated ethanol and drug from compartment 2 and would be comparable to having the drug systemically absorbed after penetrating skin layer 16 in FIG. 1 and carried away from the site of absorption by the bloodstream. The volume of each compartment is 6.5 ml.

As can be seen from the above description, the membrane separating compartments 2 and 3 simulates those which would be used in a transdermal device. Membrane I is a polypropylene membrane having a pore size of 0.1 um (Celgard membrane from Celanese Fibers Co., Summit, N.J.). Membrane II is prepared by casting a 0.1 mm layer of an medical grade adhesive film of polydimethylsiloxane blended with 18.5 w % of trichlorotrifluoroethane (355 Dow Corning medical grade adhesive, Dow Corning Corp., Midland, Mich.) on the surface of Membrane I (the polypropylene membrane). This is comparable to numerals 14 and 15 of FIG. 1. Membrane III consists of hairless mouse abdominal skin (male, six weeks old) attached to Membrane II with the epidermal layer towards Membrane II and the dermal side in contact with compartment 3. This is comparable to numeral 16 of FIG. 1. When using Membrane III, sodium azide was added to compartment 2 as an antibacterial agent (0.1 w %) to prevent bacterial degradation of the hairless mouse skin. Compartment 3, normally containing a saline solution, was connected via a pump to a saline reservoir and discharge receiver such that saline solution could be circulated through compartment 3 to prevent a buildup or saturation of drug in the saline solution. This simulates the case situation with drug flux across the skin barrier which is then systemically carried by the bloodstream into the organism to which it is administered. The temperature of the saline solution in the reservoir was maintained at about 37° C. and the flow rate of the saline through compartment 3 was about 0.1 ml/min as regulated by a peristaltic pump.

As noted and defined above, the parameters being measured by this three compartment cell are designated $P_{E1-2}$ (the amount of ethanol permeation from compartment 1 to 2 through the one-way membrane), $P_{E2-3}$ (the amount of ethanol permeation from compartment 2 to 3), $P_{W2-1}$ (the amount of water back permeation from compartment 2 to 1 through the one-way membrane), $P_{D2-1}$ (the amount of back permeation of drug from compartment 2 to 1) and $P_{D2-3}$ (the amount of drug permeation through Membranes I, II or III from compartment 2 to 3).

EXAMPLE 10

Following the procedure of Example 4, swelling measurements were performed as a function of the aqueous ethanol composition on polypropylene membrane I to show alkanol permeation capabilities. The swelling as a function of ethanol concentration in aqueous ethanol is given in Table H

TABLE H

| % Swelling | %V EtOH |
|---|---|
| 0 | 10 |
| 0 | 20 |
| 8 | 30 |
| 32 | 40 |
| 45 | 50 |
| 47 | 60 |
| 48 | 70 |

TABLE H-continued

| % Swelling | %V EtOH |
| --- | --- |
| 46 | 80 |
| 48 | 90 |
| 47 | 100 |

It will be noted that, as the ethanol composition increases, solvent uptake also increases. Minimal solvent uptake occurs below 30 v % ethanol and maximum swelling is obtained above 50 v % ethanol. This demonstrates that the hydrophobic pores in the polypropylene membranes allow preferential alkanol flux. However, alkanol flux is hindered at low alkanol composition in a binary solvent. Based on these properties of the polypropylene membrane, the ethanol composition in compartment 2 was maintained at around 40 v % unless otherwise stated in the following examples.

EXAMPLE 11

At optimum conditions in the transdermal delivery system utilizing a one-way membrane, the back flux of drug ($P_{D2-1}$) should be negligible compared with the initial amount of drug in compartment 2 and a high $P_{E1-2}$ value with a minimal $P_{W2-1}$ value should be achieved for maintaining the activity of alkanol for skin permeation and in the alkanol reservoir (compartment 1). It is also desirable to have $P_{E1-2}$ and $P_{E2-3}$ be as close to the same as possible to maintain alkanol activity in compartment 2 for a prolonged period of time. These parameters were measured under ambient conditions as a function of aqueous ethanol in compartment 2 over a period of time using the C2 one-way membrane between compartments 1 and 2 and the membrane III between compartments 2 and 3 with the results being given in Table I:

TABLE I

| V% EtOH | Permeation Rate (Mls) | | | | | | | | |
| --- | --- | --- | --- | --- | --- | --- | --- | --- | --- |
| | $P_{W2-1}$ | | | $P_{E1-2}$ | | | $P_{E2-3}$ | | |
| | 30 | 40 | 50 | 30 | 40 | 50 | 30 | 40 | 50 |
| Time (Hours) | | | | | | | | | |
| 0 | 0.0 | 0.0 | 0.0 | 0.0 | 0.0 | 0.0 | 0.0 | 0.0 | 0.0 |
| 12 | 0.0 | 0.0 | 0.0 | 0.1 | 0.2 | 0.3 | 0.1 | 0.2 | 0.3 |
| 24 | 0.0 | 0.0 | 0.0 | 0.3 | 0.5 | 0.6 | 0.2 | 0.5 | 0.8 |
| 36 | 0.0 | 0.0 | 0.0 | 0.5 | 0.6 | 0.7 | 0.4 | 0.7 | 1.0 |
| 48 | 0.0 | 0.0 | 0.02 | 0.6 | 0.8 | 0.9 | 0.5 | 0.8 | 1.3 |
| 60 | 0.0 | 0.0 | 0.03 | 0.8 | 1.2 | 1.3 | 0.6 | 1.1 | 1.6 |
| 72 | 0.0 | 0.01 | 0.04 | 1.0 | 1.5 | 1.7 | 0.7 | 1.3 | 2.0 |

It can be seen from the above that $P_{W2-1}$ is minimal in every instance at every ethanol concentration. $P_{E1-2}$ and $P_{2-3}$ compare favorably at each ethanol concentration and increase as the concentration of ethanol increases. It will be noted that $P_{E1-2}$ at the 40 and 50 v % concentration are comparable. Therefore, consistent with Example 10, the 40 v % ethanol concentration was selected as optimal in this example. However, for various systems and/or membranes, the concentration may need to be varied to obtain optimal results.

EXAMPLE 12

Based on 40 v % ethanol concentration, the effects on $P_{E2-3}$ of adding an adhesive film (Membrane II) and adhesive plus hairless mouse skin (Membrane III) to the polypropylene membrane (Membrane I) were measured over a period of time with the results being given in Table J:

TABLE J

| | $P_{E2-3}$ Permeation (Mls) | | |
| --- | --- | --- | --- |
| | Membrane I | Membrane II | Membrane III |
| Time (Hours) | | | |
| 0 | 0.0 | 0.0 | 0.0 |
| 12 | 1.8 | 0.6 | 0.3 |
| 24 | 2.3 | 1.1 | 0.5 |
| 36 | 2.6 | 1.7 | 0.7 |
| 48 | 2.9 | 2.1 | 0.8 |
| 72 | 3.4 | 2.9 | 1.4 |

It can be seen that the permeation of ethanol decreased through membrane II as compared to Membrane I as a result of the barrier effect of the medical grade adhesive film. The permeation further decreased with the addition of the hairless mouse skin as shown by Membrane III as compared to Membrane II. Because ethanol partitioning into the skin changes the lipid fluidity prior to permeation, skin shows a barrier effect against ethanol permeation.

EXAMPLE 13

It is important that an acceptable flux of drug into the skin be accomplished by means of using a device and system wherein a relatively constant feed of ethanol to the drug compartment can provide a sustained delivery of drug from the system into and through the skin. To that end, the effects of having an overlying alkanol reservoir which permits permeation of alkanol into a drug compartment for delivery to the skin is shown in the following example. Two tests were run. The first utilized a two compartment cell divided by Membrane I and the other utilized a three compartment cell wherein compartments 1 and 2 were divided by trilaminate Membrane C2 and compartments 2 and 3 were divided by Membrane I. In the two compartment cell a 40 v % ethanol was placed in compartment 1 and a saline solution in compartment 2. In the three compartment cell, neat ethanol was placed in compartment 1, 40 v % ethanol in compartment 2 and saline in compartment 3. In other words, the three compartment cell simulated a system having an overlying alkanol reservoir whereas the two compartment cell did not. Into the compartment containing the 40 v % ethanol was added 1 mg of estradiol. The permeation of estradiol as a function of time was recorded for both tests with the results being shown in Table K:

TABLE K

| | $P_{D2-3}$ Permeation (ug Estradiol) | |
| --- | --- | --- |
| Time (Hours) | Three Cell | Two Cell |
| 0 | 00 | 00 |
| 12 | 18 | 18 |
| 24 | 37 | 33 |
| 36 | 54 | 46 |
| 48 | 83 | 55 |
| 72 | 135 | 57 |

From the above it is very evident that the permeation of estradiol was greatly enhanced by having an ethanol reservoir to supply ethanol via a one-way membrane to the drug containing compartment. A relatively constant permeation rate of estradiol was obtained using a delivery system containing the ethanol reservoir. The variation of ethanol composition in compartment 2 was measured in the three cell device during the course of the test. The results indicated there was an insignificant decrease in the 40 v % ethanol composition indicating that the ethanol activity in the drug containing chamber can be maintained relatively constant using the delivery system of this invention.

EXAMPLE 14

It has been previously stated that for optical results the drug should be as soluble as possible in the alkanol solvent. The more soluble the drug is in the alkanol the greater will be the delivery to the skin. To illustrate this, the flux of estradiol through Membrane I was measured as a function of ethanol concentration in compartment 2 of the three compartment cell system with results being given in Table L:

TABLE L

| Flux [ug/cm$^2$/hr] | % V EtOH |
|---|---|
| 0.0 | 10 |
| 0.2 | 20 |
| 2.3 | 30 |
| 4.1 | 40 |

The flux increases at 30 and 40 v % ethanol due to the increased solubility of estradiol in increasing concentrations of ethanol. Similar results can be shown using testosterone and hydrocortisone. In ethanol, the solubilities of testosterone, estradiol and hydrocortisone are 0.167 g/ml, 0.036 g/ml and 0.025 g/ml respectively. Therefore, one would expect the permeated amount of testosterone to be the highest and hydrocortisone to be the lowest among these three drugs. This is due to the permeation of drug occurring through the hydrophobic pores of the polypropylene in the membrane after they have been wetted by the ethanol/water binary solvent.

The permeation rate of drug through the membrane adjacent the skin (taking into consideration the barrier effects of the membrane) should be sufficient to administer an effective amount of drug to the system of the organism to which it is being administered. Most generally, this will be a human being but may also be any warm-blooded animal to which a transdermal delivery device can be affixed. For example, the estradiol permeation rate should be at a minimum of about 0.25 ug/cm$^2$/hr. The minimum permeation rates of other drugs can be readily ascertained by those skilled in the art. Hence, the term "effective amount" may vary from drug to drug. The invention is not limited by any particular amount as it is directed to the discovery that any drug having sufficient solubility in the alkanol solvent and which can be transdermally delivered is a suitable candidate for use in the present invention.

EXAMPLE 15

As typical of the drugs which can be used, the permeated amount and flux of estradiol, testosterone and hydrocortisone over a 72 hours (three day) period are shown in the following examples. The three compartment glass cell was used. Neat ethanol was placed in compartment 1. Membrane C2 divided compartments 1 and 2. A 40 v % ethanol solution was placed in compartment 2 along with the amount of drug indicated in the tables below. Each of Membranes I, II and III were tested between compartments 2 and 3. The amount of drug ($P_{D2-3}$) permeating from compartment 2 to 3 through Membranes I, II and III was measured at 6, 12, 24, 36, 48 and 72 hours.

The drugs or solutes utilized in the following tests were 3H-estradiol, 3H-testosterone and 3H-hydrocortisone each containing a radioactive level of 300 dpm/ug. The initial amount of each drug added to the 40 v % ethanol solution of compartment 2 was 1074 ug of estradiol and testosterone and 1170 ug of hydrocortisone. The saline solution in compartment 3 was maintained at about 37° C. and circulated through that compartment at a flow rate of about 0.1 ml/min by means of a peristaltic pump. At the time intervals given in the tables which follows, 100 ul samples were withdrawn from compartment 3 and analyzed by scintillation counting for the presence of estradiol. The amounts permeated through Membranes I, II and III are reported in Tables M, N and O:

TABLE M

| | $P_{D2-3}$ Permeation (ug Estradiol) | | |
|---|---|---|---|
| Time (Hours) | Membrane I | Membrane II | Membrane III |
| 0 | 00 | 00 | 00 |
| 6 | 60 | 21 | 4 |
| 12 | 110 | 32 | 19 |
| 24 | 165 | 50 | 38 |
| 36 | 200 | 88 | 55 |
| 48 | 248 | 114 | 84 |
| 72 | 332 | 182 | 139 |

TABLE N

| | $P_{D2-3}$ Permeation (ug Testosterone) | | |
|---|---|---|---|
| Time (Hours) | Membrane I | Membrane II | Membrane III |
| 0 | 00 | 00 | 00 |
| 6 | 260 | 20 | 10 |
| 12 | 325 | 25 | 20 |
| 24 | 255 | 50 | 40 |
| 36 | 600 | 65 | 50 |
| 48 | 725 | 85 | 60 |
| 72 | 870 | 135 | 88 |

TABLE O

| | $P_{D2-3}$ Permeation (ug Hydrocortisone) | | |
|---|---|---|---|
| Time (Hours) | Membrane I | Membrane II | Membrane III |
| 0 | 00 | 00 | 00 |
| 6 | 10 | 3 | 2 |
| 12 | 22 | 8 | 6 |
| 24 | 50 | 14 | 10 |
| 36 | 70 | 20 | 15 |
| 48 | 80 | 30 | 20 |
| 72 | 110 | 45 | 30 |

From the above information the flux or permeation rate [ug/cm$^2$/hr] of each drug through each membrane can be determined over the 72 hour period. These are given in Table P:

TABLE P

| | Flux [ug/cm$^2$/hr] | | |
|---|---|---|---|
| | Membrane I | Membrane II | Membrane III |
| Estradiol | 2.72 | 1.50 | 1.14 |
| Testosterone | 7.17 | 1.10 | 0.73 |
| Hydrocortisone | 0.92 | 0.36 | 0.25 |

Shown in another way, the percentage of the initial amount of drug in compartment 2 which permeates through the Membranes I, II or III without significant variation of ethanol composition in compartment 2 is given in Table Q:

TABLE Q

| | Percent Permeation | | |
|---|---|---|---|
| | Membrane I | Membrane II | Membrane III |
| Estradiol | 31 | 17 | 12 |
| Testosterone | 81 | 12 | 8 |
| Hydrocortisone | 9.5 | 3.7 | 2.6 |

The data are consistent with the solubility of these solutes in ethanol. Testosterone, being the most soluble, shows the greatest permeation through polypropylene (Membrane I). However, it can be seen that the medical grade adhesive on a polypropylene membrane (Membrane II) has a barrier effect on solute permeation through the membrane. The permeation of solutes through Membrane III is indicative theoretically of the amounts of drug that can cross the skin. The data in the Tables M-Q show that a relatively constant permeation rate of drug can be obtained during at least a three day period when there is an overlying alkanol reservoir. This is demonstrative of the consistency between the activities of ethanol permeating the one-way membrane into the drug compartment and the permeation of drug and ethanol into the skin from the transdermal system described herein.

The data is further significant in that it shows that skin presents less of a barrier effect on solute permeation than does the adhesive film and that drug permeation is more rapid through ethanol saturated skin than through the adhesive film. Therefore, permeation through the adhesive may be the limiting factor in the formation of an acceptable delivery system utilizing an overlying solvent reservoir. The transdermal delivery system of the present invention does not require the presence of an adhesive which completely covers the membrane between the drug compartment and the skin. A suitable device might include an adhesive layer around the perimeter of the delivery device which would not require that the solute and solvent permeate the adhesive into order to come into contact with the skin.

In any event, the data in Example 15 indicates that, even in the presence of an adhesive layer adjacent the skin, acceptable flux of the drugs tested can be obtained for effective drug delivery over a sustained period of time. Therefore, the required components in the to the transdermal delivery system described herein is the overlying solvent reservoir containing a lower alkanol separated from a drug containing compartment by a one-way membrane permeable by the alkanol but substantially impermeable to drug and water. Any drug suitable for transdermal delivery may be utilized in the drug compartment as long as it has sufficient solubility in the lower alkanol to enable the alkanol to assist in the transport of the drum from the drug compartment through the outer membrane and, with the aid of the alkanol as a penetration enhancer, across the stratum corneum. The size of the system may be adapted to deliver any desired amount of drug. Obviously the greater the surface area of the system adjacent the skin the greater will be the drug delivery. This will not, however, affect the flux or delivery rate per unit of area.

The term drug or solute as contained herein describes an biologically active agent or mixture of agents having therapeutic, prophylactic or other beneficial pharmacological and/or physiological effects on the wearer of a transdermal system containing such drug or solute. Exemplary of drugs which may be used in the system are antiinflammatory drugs, analgesics, antiarthritics, antispasmodics, antidepressants, antipsychotics, tranquilizers, antianxiety agents, narcotic antagonists, antiparkinsonism agents, cholinergic agonists, anticancer agents, immunosuppressants, antivirals, antibiotics, anorexics, antiemetics, anticholinergics, antihistamines, antimigrane preparations, coronary, cerebral or peripheral vasodilators, hormonal agents, contraceptives, antithrombotics, diuretics, antihypertensive agents, cardiovascular agents and any other categories or active agents.

The active agents must be capable of transdermal or percutaneous absorption inherently or by means of an absorption enhancer. Because any transdermal device is limited somewhat in size to be acceptable to the patient it is preferable that the drug be one that is effective as low concentrations in the blood stream. Moreover, the invention is more applicable to hydrophobic categories of drugs which are soluble in the lower alkanol solvent. Examples of specific drugs are steroids such as estradiol, progesterone, testosterone, megestrol acetate, norethindrone, mestranol, corticosterone, hydrocortisone, norgestrel, levonorgestrel, medroxyprogestrone acetate and their esters, nitro-compounds such as nitroglycerine and isosorbide nitrates, nicotine, chloropheniramine, terfenadine, triprolidine, oxicam derivatives such as piroxicam, ketoprofen, mucopolysaccharidases such as thiomucase, buprenorphine, fentanyl, naloxone, codeine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapmil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions and the salts of such compounds with pharmaceutically acceptable acids or bases.

Other agents meeting the above described criteria for percutaneous absorbability, and alkanol solubility may be utilized without departing from the scope of the invention. Also, other modifications may be made by those familiar with the transdermal delivery of drugs. For example, the one-way membrane could be made of other materials provided it allows for the permeation of the alkanol solvent into the drug compartment at an acceptable rate and prevents the back flux of drugs and water. The other parts of the system, i.e. the walls and roof of the solvent reservoir and walls of the drug compartment may be made of any suitable material which is inert to the drug, solvent, water or any other materials which may be contained in the system. The invention is therefore limited only in scope by the appended claims and their functional equivalents.

We claim:

1. A dual compartment system for transdermally delivering an active agent to the skin of a wearer comprising:

(a) a solvent reservoir compartment defined by walls and one closed and one open end and containing ethanol as a solvent, (b) a drug compartment having walls and opposing open ends and containing said active agent, (c) an epoxidized silicone rubber containing membrane having opposing surfaces, one surface being attached to and overlying the open end of said solvent reservoir compartment and the other surface being attached to and overlying one open end of said drug compartment thereby separating said solvent reservoir from said drug compartment by said membrane, said membrane being permeable to ethanol from said solvent reservoir and substantially impermeable to drug and water from said drug compartment; and (d) a second membrane having opposing surfaces and being permeable to said ethanol and drug, one surface being attached to and overlying the other open end of said drug compartment said second membrane having adhesive means on the other surface thereof for attaching said delivery system to the skin of a wearer.

2. A delivery system according to claim 1 wherein said epoxidized silicone rubber containing membrane is an epoxidized silicon rubber consisting of a copolymer of about 90–98% w a polydimethyl siloxane and about 2–10% w of a polyglycerol-polyglycidyl ether.

3. A delivery system according to claim 2 wherein said polyglycerol-polyglycidyl ether has the formula $$\begin{array}{c}CH_2-O+CH_2-CH-CH_2-O-CH_2-CH-CH_2-O\!\!\!\!\!\!\!/_{\overline{z}}CH_2\\ |\qquad\qquad |\qquad\qquad\qquad\qquad |\qquad\qquad\qquad |\\ CH\qquad\quad OH\qquad\qquad\qquad O\qquad\qquad CH\\ \diagdown O\qquad\qquad\qquad\qquad\qquad CH_2\qquad\qquad \diagdown O\\ /\qquad\qquad\qquad\qquad\qquad\qquad |\qquad\qquad\qquad /\\ CH_2\qquad\qquad\qquad\qquad\qquad CH\qquad\qquad CH_2\\ \qquad\qquad\qquad\qquad\qquad\qquad\diagdown O\\ \qquad\qquad\qquad\qquad\qquad\qquad /\\ \qquad\qquad\qquad\qquad\qquad\qquad CH_2\end{array}$$

wherein z is an integer of 2 to 3.

4. A delivery system according to claim 3 wherein said epoxidized silicone rubber containing membrane is a bilaminate consisting of a layer of said epoxidized silicone rubber and a layer of a dense hydrophobic copolymer of vinyl-terminated polydimethyl siloxane with methylhydro-dimethyl siloxane.

5. A delivery system according to claim 4 wherein said dense hydrophobic copolymer contains about 90 to 98% w. of the vinyl-terminated polydimethyl siloxane and about 2 to 10% w. of the methylhydro-dimethyl siloxane.

6. A delivery system according to claim 5 wherein said epoxidized silicone rubber containing membrane has a thickness of between about 0.4 and 1.0 mm and wherein said epoxidized silicone rubber portion of the membrane faces the solvent reservoir and the dense hydrophobic copolymer portion of the membrane faces the drug compartment.

7. A delivery system according to claim 6 wherein said epoxidized silicone rubber portion of said epoxidized silicone rubber containing membrane is thicker than said dense hydrophobic copolymer portion of said membrane.

8. A delivery system according to claim 7 wherein said active agent is soluble in said ethanol solvent.

9. A delivery system according to claim 1 wherein said drug compartment contains said active agent and aqueous ethanol.

10. A delivery system according to claim 3 wherein said epoxidized silicone rubber containing membrane is a trilaminate consisting of a layer of said epoxidized silicone rubber, an intermediate layer of cellulose acetate and a layer of a dense hydrophobic copolymer of vinyl-terminated polydimethyl siloxane with methylhydro-dimethyl siloxane.

11. A delivery system according to claim 10 wherein said dense hydrophobic copolymer contains about 90 to 98% w. of the vinyl-terminated polydimethyl siloxane and about 2 to 10% w. of the methylhydro-dimethyl siloxane.

12. A delivery system according to claim 11 wherein said epoxidized silicone rubber containing membrane has a thickness of between about 0.4 and 1.0 mm and wherein said epoxidized silicone rubber portion of the membrane faces the solvent reservoir and the dense hydrophobic copolymer portion of the membrane faces the drug compartment.

13. A delivery system according to claim 12 wherein said epoxidized silicone rubber portion of said epoxidized silicone rubber containing membrane is thicker than said dense hydrophobic copolymer portion of said membrane.

14. A delivery system according to claim 13 wherein said cellulose acetate layer has a thickness of about 10 to 50 microns.

15. A delivery system according to claim 14 wherein said active agent is soluble in said ethanol solvent.

16. A delivery system according to claim 1 wherein said drug compartment contains said active agent and aqueous ethanol.

17. A delivery system according to claim 16 wherein said active agent is a hydrophobic drug.

18. A silicone rubber containing membrane permeable to lower alkanol solvents and substantially impermeable to water and hydrophobic solutes comprising (a) a first layer comprising an epoxidized silicone rubber consisting of a copolymer of about 90–98% w a polydimethyl siloxane and about 2–10% w of a polyglycerol-polyglycidyl ether having the formula $$\begin{array}{c}CH_2-O+CH_2-CH-CH_2-O-CH_2-CH-CH_2-O\!\!\!\!\!\!\!/_{\overline{z}}CH_2\\ |\qquad\qquad |\qquad\qquad\qquad\qquad |\qquad\qquad\qquad |\\ CH\qquad\quad OH\qquad\qquad\qquad O\qquad\qquad CH\\ \diagdown O\qquad\qquad\qquad\qquad\qquad CH_2\qquad\qquad \diagdown O\\ /\qquad\qquad\qquad\qquad\qquad\qquad |\qquad\qquad\qquad /\\ CH_2\qquad\qquad\qquad\qquad\qquad CH\qquad\qquad CH_2\\ \qquad\qquad\qquad\qquad\qquad\qquad\diagdown O\\ \qquad\qquad\qquad\qquad\qquad\qquad /\\ \qquad\qquad\qquad\qquad\qquad\qquad CH_2\end{array}$$

wherein z is an integer of 2 or 3, and (b) a second layer of a dense hydrophobic copolymer containing about 90 to 98% w. of the vinyl-terminated polydimethyl siloxane and about 2 to 10% w. of the methylhydro-dimethyl siloxane.

19. A silicone rubber containing membrane according to claim 1 wherein said epoxidized silicone rubber first layer portion of said silicone rubber containing membrane is thicker than said dense hydrophobic copolymer second layer portion of said membrane.

20. A silicone rubber containing membrane according to claim 19 wherein said membrane has a thickness of between about 0.4 and 1.0 mm and wherein the epoxidized silicone rubber first layer portion is about twice as thick as said dense hydrophobic copolymer second layer portion.

21. A silicone rubber containing membrane according to claim 19 containing a layer of hydrophilic cellulose acetate sandwiched between said epoxidized silicone rubber first layer portion and said dense hydrophobic copolymer second layer portion.

22. A silicone rubber containing membrane according to claim 21 wherein said cellulose layer has a thickness of between about 10 and 50 microns.

* * * * *